(12) United States Patent
Rapin et al.

(10) Patent No.: US 7,163,922 B2
(45) Date of Patent: Jan. 16, 2007

(54) TRIPEPTIDE DERIVATIVES FOR THE TREATMENT OF POSTLESIONAL DISEASES OF THE NERVOUS SYSTEM

(75) Inventors: Jean Rapin, Paris (FR); Hans Klaus Witzmann, Egglkofen (DE); Jean-Marie Grumel, Tassin la Demi-Lune (FR); Jacques Gonella, Muttenz (CH)

(73) Assignee: Neurotell AG, Hergiswil (CH)

( * ) Notice: Subject to any disclaimer, the term of this patent is extended or adjusted under 35 U.S.C. 154(b) by 0 days.

(21) Appl. No.: 10/635,808

(22) Filed: Aug. 5, 2003

(65) Prior Publication Data

US 2005/0101539 A1   May 12, 2005

Related U.S. Application Data

(63) Continuation of application No. PCT/EP02/01182, filed on Feb. 5, 2002.

(51) Int. Cl.
A61K 38/00 (2006.01)
(52) U.S. Cl. .................................................. 514/18
(58) Field of Classification Search ................ 514/18; 530/330, 331, 338
See application file for complete search history.

(56) References Cited

U.S. PATENT DOCUMENTS

| | | | | |
|---|---|---|---|---|
| 4,985,428 A * | 1/1991 | Carenzi et al. | ............... | 514/18 |
| 5,043,346 A * | 8/1991 | Hock et al. | ................. | 514/409 |
| 5,212,158 A | 5/1993 | Vandai | | |
| 5,840,838 A * | 11/1998 | Hensley et al. | ............ | 530/324 |
| 5,973,111 A | 10/1999 | Bemis et al. | | |
| 6,080,848 A * | 6/2000 | Henrichwark et al. | ..... | 536/23.5 |
| 6,156,572 A | 12/2000 | Bellamkonda et al. | | |
| 6,235,929 B1 | 5/2001 | Powers | | |
| 6,645,518 B1 * | 11/2003 | Tedeschi et al. | ............ | 424/423 |

FOREIGN PATENT DOCUMENTS

| | | |
|---|---|---|
| EP | 0316218 A1 | 5/1989 |
| EP | 0446706 A2 | 9/1991 |
| EP | 0446706 A3 | 9/1991 |
| EP | 1018341 A | 7/2000 |
| EP | 1231279 A1 | 8/2002 |
| JP | 04-005240 A | 1/1992 |
| WO | WO 88/09604 A2 | 12/1988 |
| WO | WO 92/11850 A2 | 7/1992 |
| WO | WO 92/13549 * | 8/1992 |
| WO | WO 96/41638 A1 | 12/1996 |
| WO | WO 98/14202 A1 | 4/1998 |
| WO | WO 01/28578 A2 | 4/2001 |
| WO | WO 01/28578 A3 | 4/2001 |
| WO | WO 01/34828 A1 | 5/2001 |
| WO | WO 01/68114 A1 | 9/2001 |
| WO | WO 02/062373 A2 | 8/2002 |
| WO | WO 02/062373 A3 | 8/2002 |
| WO | WO 02/062828 A2 | 8/2002 |
| WO | WO 02/062828 A3 | 8/2002 |

OTHER PUBLICATIONS del Zoppo et al. Trends and Future Developments in the Pharmacological Treatment of Acute Ischaemic Stroke. Drugs. Jul. 1997, vol. 54, No. 1, pp. 9-38.*
Kan. Current and future approaches to therapy of Alzheimer's disease. Eur J Med Chem 1992, vol. 27, pp. 565-570.*
Nabeshima et al., Staurosporine, a protein kinase inhibitor, attenuates basal forebrain-lesion-induced amnesia and cholinergic neuronal deficit. Neuroscience Letters 1990 vol. 122, pp. 13-16.*
Amnesia: Online References For Health Concerns. Accessed online via http://www.lef.org/protocols/prtcl-007.shtml on May 4, 2005. pp. 1-2.*
Definition of 'shock': http://www.answers.com/shock, accessed online Dec. 8, 2005, 1 page.*
Definition and thesaurus of 'impact': http://www.answers.com/impact, accessed online Dec. 10, 2005, 2 pages.*
Definition of 'trauma': http://www.answers.com/trauma, accessed online Dec. 10, 2005, 1 page.*
Faden, A.I., et al., "Effect of TRH analogs on neurologic recovery after experimental spinal trauma," *Neurology*, 35:1331-1334 (1985).
Geschwind, M., et al., "Detection of apoptotic or necrotic death in neuronal cells by morphological, biochemical, and molecular analysis," in *Apoptosis Techniques and Protocols*, J. Poirier, ed., 1997, pp. 13-31.
Guiloff, R.J., "Thyrotropin releasing hormone and motorneurone disease", *Reviews in the Neurosciences*, 1:201-219 (1987).
Kurtz, A.F., "Praktische Diagnostik," in *Aktuelles Wissen Hoechst, Alzheimer-Patienten erkennen und behandeln*, Hoechst AG, publisher (Munich, Germany, 1995), 68-69. With partial translation.
Rapin, J.R., "Les nootropes: propiétés pharmacologiques du piracétam et indications thérapeutiques," *La Lettre du Pharmacologue*, 6(5):108-111 (1992). With partial translation.

(Continued)

Primary Examiner—Anish Gupta
Assistant Examiner—Marcela M Cordero Garcia
(74) Attorney, Agent, or Firm—Clark G. Sullivan; King & Spalding

(57) ABSTRACT

The invention relates to the use of specific tripeptides for the treatment of postlesional diseases of ischemic, traumatic or toxic origin. The tripeptide derivatives satisfy formula (I), wherein X represents OH, $(C_{1-5})$alkoxy, $NH_2$, $NH-C_{1-5}$-alkyl, $N(C_{1-5}$ alkyl$)_2$; $R_1$ is a residue derived from any of the amino acids Phe, Tyr, Trp, Pro, each of which may optionally be substituted by a $(C_{1-5})$ alkoxy group, a $(C_{1-5})$ alkyl group or a halogen atom, and Ala, Val, Leu, or Ile; $R_2$ is a residue which is derived from any of the amino acids Gly, Ala, Ile, Val, Ser, Thr, His, Arg, Lys, Pro, Glu, Gln, pGlu, Asp, Leu and Asn; $R_3$ and $R_4$ independently represent H, OH, (C1–C5) alkyl, or $(C_{1-5})$alkoxy, provided that $R_3$ and $R_4$ are not both OH or $(C_{1-5})$alkoxy; $R_5$ represents H, OH, $(C_{1-5})$alkyl or $(C_{1-5})$alkoxy; and wherein $R_0$ preferably represents a cinnamoyl residue; or pharmaceutically acceptable salts thereof.

4 Claims, No Drawings

OTHER PUBLICATIONS

Sarti, G., et al., "TRH-analogues: A possible treatment for symptoms of dementia in elderly patients?", *Archives of Gerontology and Geriatrics*, 12:173-177 (1991).

Szirtes, T., et al., "Synthesis of thyrotropin-releasing hormone analogues. 1. Complete dissociation of central nervous system effects from thyrotropin-releasing actvity," *J. Med. Chem.* 27:741-745 (1984).

Beyer, H., and Walter, W., *Handbook of Organic Chemistry*, by S. Hirzel Verlag, Stuttgard (English translation of the 22$^{nd}$ edition of *Lehrbuch der Organischen Chemie*) (1996), pp. 827-838.

Blundell, T.L., et al., "Knowledge-based protein modelling and design", *Eur. J. Biochem.*, 172:513-520 (1988).

Cheesebeuf, M., et al., "Rat liver epithelial cell cultures in a serum-free medium: primary cultures and derived cell lines expressing differentiated functions", *In Vitro*, 20(10):780-795 (1984).

Clark, M.C., et al., "Validation of the general purpose Tripos 5.2 force field", *J. Comp. Chem.*, 10(8):982-1012 (1999).

De Pooter, H., et al., "N-acylamino acids and peptides IV the synthesis of N-cinnamyl-, N-p.coumaryl- and N-caffeyl-glycine and -glycyl-L-phenylalanine", *Bull. Soc. Chim. Belg.*, 85(9):647-656 (1976). XP008015013.

Faden, A.I., et al., "Novel TRH analog improves motor and cognitive recovery after traumatic brain injury in rodents", *Amer. J. Physiology* 277(4, pt. 2):R1196-R1204 (1999), *Chem. Abstr.* 132:31033 XP002207513, XP008014976.

Faden, A.I., et al., "Structure-activity relationships of TRH analogs in rat spinal cord injury", *Brain Research*, 448:287-293 (1988). XP008015202.

Gasteiger, J., et al., "Iterative partial equalization of orbital electronegativity—a rapid access to atomic charges", *Tatrahedron*, 36:3219-3238 (1980).

Hagg, T., et al., "Delayed treatment with nerve growth factor reverses the apparent loss of cholinergic neurons after acute brain damage", *Exp. Neurol.*, 101:303-312 (1988).

Jones, D.T., et al., "A new approach to protein fold recognition", *Nature*, 358:86-89 (Jul. 1992).

Jones, D.T., "Protein secondary structure prediction based on position-specific scoring matrices", *J. Mol. Biol.*, 292(2):195-202 (1999).

Kansy, M., et al. "Physicochemical High Throughput Screening: Parallel Artificial Membrane Permeation Assay in the Description of Passive Absorption Processes", *J. Med. Chem.*, 41(7):1007-1010 (Mar. 26, 1998).

Khuebachova, M., et al., "Mapping the C terminal epitope of the Alzheimer's disease specific antibody MN423", *J. Immunol. Methods* (Elsevier Amsterdam, NL) 262(1-2):205-215 (2002). XP004352190.

Laskowski, R.A., et al., "Procheck: a program to check the stereochemical quality of protein structures", *J. Appl. Cryst.*, 26:283-291 (1993).

Le Poncin-Lafitte, M., et al., "Sound-avoidance conditioning and a mathematical approach to the description of acquisition performance", *Math. Biosciences*, 59:249-268 (1982).

Luco, J.M., "Prediction of the brain-blood distribution of a large set of drugs from structurally derived descriptors using partial least-squares (PLS) modeling", *J. Chem.. Inf. Comput. Sci.*, 39 (2):396-404 (1999).

Parnetti, L., et al., "Posatirelin for the treatment of late-onset Alzheimer's disease: a double-blind multicentre study vs citicoline and ascorbic acid", *Acta Neurol. Scand.* 92:135-140 (1995).

Varon, S., et al., "Nerve Growth Factor in CNS Repair", *J. Neurotrama*, 11(5) (1994).

Wang. R., et al., "SCORE: A new empirical method for estimating the binding affinity of a protein-ligand complex", *J. Mol. Model.*, 4:379-394 (1998).

Weiner, S.J., et al., "A new force field for molecular mechanical simulation of nucleic acids and proteins", *J. Am. Chem. Soc.*, 106:765-784 (1984).

Wiesman, C., et al., "Crystal structure of nerve growth factor in complex with the ligand-binding domain of the TrkA receptor", *Nature*, 401:184 (Sep. 9, 1999).

\* cited by examiner

TRIPEPTIDE DERIVATIVES FOR THE TREATMENT OF POSTLESIONAL DISEASES OF THE NERVOUS SYSTEM

This application is a continuation, under 35 U.S.C. §365 (c), of the PCT patent application entitled "Tripeptide Derivatives for the Treatment of Postlesional Diseases of the Nervous System," having International Application No. PCT/EP02/01182, International Filing Date of 5 Feb. 2002 (05.02.2002), and Priority Date of 5 Feb. 2001 (05.02.2001), which claims priority to German Patent Application No. 101 05 040.2, filed on 5 Feb. 2001, the disclosures of which are entirely incorporated herein by reference.

The invention relates to the use of tripeptide derivatives for the treatment of postlesional diseases of the nervous system, particularly those of necrotic origin such as e.g. ischemia, trauma or intoxication.

BACKGROUND ART

Ischemia of nerves or of nervous tissue is generally caused by vascular diseases, e.g. due to embolism or a thrombosis. The nerves of the central nervous system may be effected thereby, e.g. by a cerebral infarction. Ischemia ultimately leads to the necrotic death of the affected tissue.

A traumatic impact may also lead to such a death of the nerves. For example, spinal cord injuries and mechanical lesions of peripheral nerves are known. Moreover, environmental influences due to toxic substances, e.g. heavy metals, may result in a necrosis of nerves.

New therapeutic approaches for such nerve injuries comprise the administration of neurotrophic factors or of neurotrophines to which a significant influence on the survival, growth and differentiation of discrete neuronal populations is ascribed. The neurotrophine family includes nerve growth factor (NGF), brain derived neurotrophic factor (BDNF), neurotrophine-3 (NT-3), neurotrophine-4 (NT-4) and the CNTF-family (ciliary neurotrophic factor). Neurotrophines are small basic proteins with a molecular weight of 26 to 28 kDa. NGF is the best characterised member of the neurotrophine family which shows activity in many different tissues.

In the peripheral nervous system (PNS) NGF is critical to the development of sympathetic and certain sensory nerves. In the central nervous system (CNS), NGF serves a trophic role in the development and maintenance of cholinergic neurons of the basal forebrain. It also plays a role in adult CNS tissues in neuronal regeneration.

The use of neurotrophic factors for the treatment of postlesional neuronal diseases of e.g. traumatic, ischemic or toxic origin has not attained the expected success up to now.

Particularly in the case of the treatment of nerve injuries in the brain, neurotrophic factors are not suitable since they may not pass the blood-brain barrier and are thus not available for parenteral or enteral administration.

The stimulatory effect on nerve growth required for the treatment of postlesional diseases is to be distinguished from a nootropic effect of substances, as described for example in EP 0 316 218 B1, which is only observed temporarily during administration, but does not provide a permanent nerve regeneration.

SUMMARY OF THE INVENTION

Therefore, it is the object underlying the present invention to provide substances which stimulate nerve growth and are thus suitable for the treatment of postlesional neuronal diseases as e.g. those of ischemic, traumatic or toxic origin.

This object of the present invention is solved by the use of compounds of the following formula (I):

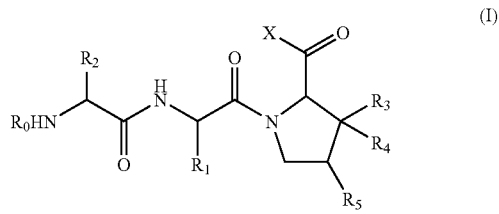

wherein X represents OH, $(C_{1-5})$alkoxy, $NH_2$, $NH$—$C_{1-5}$-alkyl, $N(C_{1-5}$ alkyl$)_2$;

$R_1$ is a residue derived from any of the amino acids Phe, Tyr, Trp, Pro, each of which may optionally be substituted by a $(C_{1-5})$ alkoxy group, a $(C_{1-5})$ alkyl group or a halogen atom, and Ala, Val, Leu, or Ile;

$R_2$ is a residue which is derived from any of the amino acids Gly, Ala, Ile, Val, Ser, Thr, His, Arg, Lys, Pro, Glu, Gln, pGlu, Asp, Leu and Asn;

$R_3$ and $R_4$ independently represent H, OH, $(C_1$-$C_5)$alkyl, or $(C_{1-5})$alkoxy, provided that $R_3$ and $R_4$ are not both OH or $(C_{1-5})$alkoxy;

$R_5$ represents H, OH, $(C_{1-5})$ alkyl or $(C_{1-5})$alkoxy;

and wherein $R_0$ represents a group of the formula

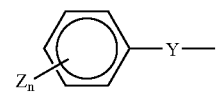

wherein Y represents —CO—, —$CH_2CO$—, —$CH_2CH_2CO$—, —$CH_2CH_2CH_2CO$—, —CH═CH—CO or —$OCH_2CO$—, and wherein Z represents a halogen atom, a trifluormethyl group, $(C_{1-4})$ alkoxy group, $(C_{1-4})$ alkyl group; or wherein two neighbouring substituents may form a $(C_{1-3})$ alkylenedioxy group; and wherein n is 0 or an integer of from 1 to 5;

or pharmaceutically acceptable salts thereof;

for the preparation of a medicament useful in the treatment of postlesional diseases of ischemic, traumatic or toxic origin.

DETAILED DESCRIPTION

If not indicated otherwise, the amino acid residues may be present both in the D-form as well as the L-form, the L-form being preferred.

Preferred are compounds of the formula (I) in which $R_1$ is a residue derived from the amino acid Ile or one of the amino acids Phe, Tyr, Trp, which each may be optionally substituted with one or more $(C_{1-5})$ alkoxy groups, $(C_{1-5})$ alkyl groups or one or more halogen atoms, particularly a residue which is derived from Ile or Phe which is optionally substituted with one or more $(C_{1-5})$ alkoxy groups, $(C_{1-5})$ alkyl groups or one or more halogen atoms.

In formula (I), X is preferably $(C_{1-5})$ alkoxy, $NH_2$, $NH$—$(C_{1-5})$ alkyl or $N(C_{1-5}$ alkyl$)_2$, more preferred are $NH_2$, $NH(C_{1-3})$ alkyl and $N(C_{1-3}$ alkyl$)_2$.

$R_2$ is preferably a residue derived from the amino acid Gly or Ile.

$R_3$ and $R_4$ preferably independently from each other represent H, $(C_{1-5})$ alkyl or $(C_{1-5})$ alkoxy, provided that $R_3$ and $R_4$ are not $(C_{1-5})$ alkoxy, more preferred are H, $(C_{1-3})$ alkyl or $(C_{1-3})$ alkoxy.

$R_5$ preferably represents H, $(C_{1-5})$ alkyl or $(C_{1-5})$ alkoxy, particularly preferred are H, $(C_{1-3})$ alkyl or $(C_{1-3})$ alkoxy.

$R_0$ is preferably a cinnamoyl residue.

For particularly preferred compounds of formula (I), $R_0$ is preferably a cinnamoyl residue, $R_1$ is a residue which is derived from Phe which is optionally substituted with one or more $(C_{1-5})$ alkoxy groups, $(C_{1-5})$ alkyl groups or one or more halogen atoms, or which is derived from the amino acid Ile, $R_2$ is a residue derived from the amino acid Gly or Ile, $R_3$, $R_4$ and $R_5$ represent a hydrogen atom, X is $NH_2$, $NH$—$(C_{1-3})$ alkyl or $N(C_{1-3}$ alkyl$)_2$.

Most preferred compounds of formula (I) are cinnamoyl-glycyl-L-phenylalanyl-L-prolineamide, cinnamoyl-isoleucyl-phenylalanyl-L-proline ethylamide, cinnamoyl-isoleucyl-isoleucyl-prolineamide, or a pharmaceutically acceptable salt thereof.

The abbreviations used for the amino acids (Phe for phenylalanine etc. as well as partially the one-letter-codes used below, such as F for phenylalanine) are known to the skilled person (see e.g. Beyer and Walter, Lehrbuch der Organischen Chemie, 21st edition, S. Hirzel Verlag Stuttgart 1988). Hence, Phe means phenylalanine, Gly glycine etc. The expression "a residue derived from the amino acid Phe" thus means a benzyl (—$CH_2$—$C_6H_5$) residue. Accordingly, "a residue derived from the amino acid Gly" means a hydrogen atom, "a residue derived from the amino acid Ala" a methyl group etc.

The synthesis of the tripeptide derivatives used according to the present invention is not particularly limited and can be carried out according to known methods, preferably stereospecific processes of peptide chemistry in which the L- or D-configuration of the respective amino acids or their derivatives is maintained. Particularly suitable are the syntheses disclosed in EP 0 316 218 B1.

The compounds of formula (I) used according to the present invention are lipophilic substances and suitable for enteral and in appropriate formulations for parenteral administration.

An administration in a dose of 1 to 5 mg per kilogram bodyweight per day, preferably 75 to 375 mg per day is usually effective. To achieve the neuro-regenerative effect, an administration over several days (for example at least 4 or 5 days) is generally preferred.

The tripeptide derivatives to be used according to the present invention show a very low toxicity. In mice, using dosages of up to 1000 mg/kg p.o. according to the Irwin test, no lethal or cramp causing effects were observed.

The tripeptide derivatives may be used for the production of pharmaceutical compositions which are suitable for administration in different ways, e.g. parenteral (intravenous, intramuscular, subcutane), via the respiratory tract (buccal, sublingual, nasal, bronchial), the transdermal route (percutane) and the enteral route (peroral).

The pharmaceutical compositions of the present invention further contain a pharmaceutically acceptable excipient, pharmaceutically acceptable diluents or adjuvants. Standard techniques may be used for their formulation, as e.g. disclosed in Remington's Pharmaceutical Sciences, 20$^{th}$ edition Williams&Wilkins, Pa. USA.

The administration form is selected depending on the administration route and comprises inter alia tablets, capsules, powders and solutions.

For oral administration, tablets and capsules are preferably used which contain a suitable binding agent, e.g. gelatine or polyvinyl pyrrolidone, a suitable filler, e.g. lactose or starch, a suitable lubricant, e.g. magnesium stearate, and optionally further additives. Preferred are formulations containing 75 to 225 mg, more preferably 100 to 200 mg, of the tripeptide derivate per administration unit, e.g. per tablet or capsule.

A particularly preferred formulation for oral administration is a coated tablet containing 100 mg Cinnamoyl-Gly-Phe-ProNH$_2$ as well as microcristalline cellulose, maize starch, Povidon 25, Crospovidon, Macrogol 4000, titanium dioxide (E171), and ferric oxide (E172).

For parenteral administration, sterile ethanol-containing aqueous solutions are preferred. Suitable sterile aqueous solutions or physiological saline solution may contain 10% v/v ethanol. A volume of 10 ml of such a solution is used to dissolve 100 mg of lyophilised Cinnamoyl-Gly-Phe-ProNH$_2$, in an appropriate medical device for injection.

Particularly for treating spinal cord injuries and mechanical lesions of peripheral nerves, implantation of a material to which the compounds to be used according to the present invention have been immobilized, is a suitable method of ensuring guided nerve regrowth. Different methods of immobilization of peptides to a wide variety of materials are known (for references, see U.S. Pat. No. 6,156,572). According to the present invention, it is thus particularly preferred to immobilize the compounds of formula (I) on a biocompatible and possibly biodegradable material, such as hydrogels, preferably polysaccharide hydrogels, such as agarose, alginate or chitosan, or poly(lactide), polyethylene oxide, and hyaluronate. Immobilization methods of the peptides to these materials are known to the skilled person and include typical activation steps of hydroxyl groups for forming amide bonds, such as carbodiimide activation, such as EDC activation, or the use of a bi-functional imidazole coupling agent, e.g. 1,1'-carbonyldiimidazole. The tripeptide derivatives to be used according to the present invention are preferably immobilized at the group R, which is preferably a cinnamoyl group. Suitable immobilization reactions include a photochemical reaction of the cinnamoyl group with alkenyl groups on the immobilization matrix. Particularly useful immobilization matrices are disclosed in U.S. Pat. No. 6,156,572. The polysaccharides used as matrix may be derivatized using alkenyl groups such as cinnamoyl groups allowing the photochemical coupling.

The neuro-regenerative effect of the tripeptide derivatives to be used according to the present invention is surprising, particularly when administered parenterally or enterally. Although the nootropic effect of these substances is known from EP 0 316 218 B1, the finding that these substances do not only show a temporary nootropic effect during administration, but a permanent nerve regeneration could not be expected.

The neuro-regenerative properties of the tripeptide derivatives used according to the present invention will be demonstrated in a neurite growth assay. Using this assay, it could be demonstrated that the administration of the tripeptide derivatives results in a significant increase in the formation of neurites.

Experiment

The sprouting of nerve cells is determined by the length of the dendrites. According to the present invention, the influence of the substances used according to the present invention on the sprouting is studied in an in vivo assay.

The septum of the hippocampus of 10 rats was destroyed (see Hagg et al; Exp. Neurol., 101, 303–312). 21 days after the impairment of the hippocampus was unambiguous, as confirmed by a behavioural test, the rats were divided into two groups of 5 rats each. 10 mg/per kg bodyweight per day of the substance used according to the present invention (Cinnamoyl-GFPNH$_2$) was administered to the test group of 5 rats over at least 15 days.

After administration, the animals were killed, and the cholinergic nerve ends were observed by a CAT (choline-acetyl-transferase) immunofluorescence assay under a fluorescence microscope. The length of the dendrites was measured thereby.

In the rats of the control group, a change of the dendrite length of up to 2 μm was observed. On the other hand, the administration of the substance used according to the present invention resulted in an increase of the dendrite length of up to 8 to 10 μm in the test group. Hence, Cinnamoyl-GFPNH$_2$ is a growth factor resulting in the growth of dendrites.

What is claimed is:

1. A method for the treatment of a postlesional neuronal disease due to cerebral infarction or traumatic impact characterized by nerve cell necrosis, thereby effecting nerve regeneration, comprising administering an effective amount of a compound to stimulate nerve growth, wherein the compound is of formula (I):

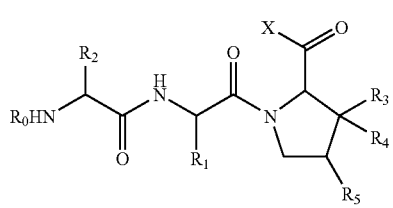

(I)

wherein X represents NH$_2$, NH—(C$_{1-3}$)alkyl or N(C$_{1-3}$alkyl)$_2$;

R$_1$ is a residue derived from the amino acid Phe which may optionally be substituted with one or more methoxy groups, or methyl groups or one or more halogen atoms; or is derived from the amino acid Ile;

R$_2$ is a residue which is derived from any one of the amino acids Gly or Ile;

R$_3$-and R$_4$ independently represent H;

R$_5$ represents H;

and wherein R$_0$ represents a group of the formula

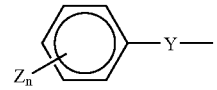

wherein Y represents —CO—, —CH$_2$CO—, —CH═CH—CO— or —OCH$_2$CO—, and wherein Z represents a halogen atom, a trifluormethyl group, a methoxy group, or a methyl group; or wherein two neighbouring substituents may form a (C$_{1-3}$) alkylendioxy group; and wherein n is 0 or an integer of from 1 to 5;

or a pharmaceutically acceptable salt thereof.

2. The method according to claim 1, wherein R$_1$ is a residue derived from Phe which may optionally be substituted by with one or more methoxy groups, or methyl groups or one or more halogen atoms.

3. The method according to claim 1, wherein R$_0$ is a cinnamoyl moiety.

4. The method according to claim 1, wherein the compound of formula (I) is cinnamoyl-glycyl-L-phenylalanyl-L-prolinamide, cinnamoyl-isoleucyl-phenylalanyl-L-proline ethylamide, cinnamoyl-isoleucyl-isoleucyl-prolineamide, or a pharmaceutically acceptable salt thereof.

* * * * *